(12) United States Patent
Perianin et al.

(10) Patent No.: US 10,201,536 B2
(45) Date of Patent: Feb. 12, 2019

(54) METHODS AND PHARMACEUTICAL COMPOSITIONS FOR THE TREATMENT OF BACTERIAL INFECTIONS IN PATIENTS SUFFERING FROM CIRRHOSIS

(71) Applicants: INSERM (INSTITUT NATIONAL DE LA SANTE ET DE LA RECHERCHE MEDICALE), Paris (FR); UNIVERISTE PARIS DIDEROT—PARIS 7, Paris (FR); CENTRE NATIONAL DE LA RECHERCHE SCIENTIFIQUE (CNRS), Paris (FR)

(72) Inventors: Axel Joseph Perianin, Paris (FR); Loiec Rolas, Paris (FR)

(73) Assignees: INSERM (INSTITUT NATIONAL DE LA SANTE ET DE LA RECHERCHE MEDICALE), Paris (FR); UNIVERISTE PARIS DIDEROT—PARIS 7, Paris (FR); CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 0 days.

(21) Appl. No.: 15/571,971

(22) PCT Filed: May 12, 2016

(86) PCT No.: PCT/EP2016/060762
§ 371 (c)(1),
(2) Date: Nov. 6, 2017

(87) PCT Pub. No.: WO2016/180945
PCT Pub. Date: Nov. 17, 2016

(65) Prior Publication Data
US 2018/0140597 A1 May 24, 2018

(30) Foreign Application Priority Data

May 12, 2015 (EP) .................................... 15305716
Dec. 2, 2015 (EP) .................................... 15306912

(51) Int. Cl.
*A61K 9/14* (2006.01)
*A61K 45/06* (2006.01)
*A61P 31/04* (2006.01)
*A61K 31/4745* (2006.01)

(52) U.S. Cl.
CPC ............ *A61K 31/4745* (2013.01); *A61K 9/14* (2013.01); *A61K 45/06* (2013.01); *A61P 31/04* (2018.01)

(58) Field of Classification Search
CPC .................................................. A61K 31/4745
USPC .......................................................... 514/293
See application file for complete search history.

(56) References Cited

U.S. PATENT DOCUMENTS

2012/0128715 A1 5/2012 Levy et al.

FOREIGN PATENT DOCUMENTS

WO 2015/011254 A1 1/2015
WO WO-2015011254 A1 * 1/2015 ........... A61K 38/164

OTHER PUBLICATIONS

Sallenave, "Antimicrobial activity of antiproteinases", Biochemical Society Transactions, vol. 30, No. 2, p. 111-115 (2002).*
Jalan Rajiv et al: "Bacterial infections in cirrhosis: A position statement based on the EASL Special Conference 2013", Journal of Hepatology, Elsevier, Amsterdam, NL, vol. 60, No. 6, pp. 1310-1324, Feb. 12, 2014.
K. Makni-Maalej et al: "The TLR7/8 Agonist CL097 Primes N-Formyl-Methionyl-Leucyl-Phenylalanine-STimulated NADPH Oxidase Activation in Human Neutrophils: Critical Role of p47phox Phosphorylation and the Proline Isomerasz Pin1", The Journal of Immunology, vol. 189, No. 9, pp. 4657-4665, Sep. 21, 2012.

* cited by examiner

Primary Examiner — Kevin E Weddington
(74) Attorney, Agent, or Firm — Whitham & Cook, P.C.

(57) ABSTRACT

The present invention relates to methods and pharmaceutical compositions for the treatment of bacterial infections in patients suffering from cirrhosis. In particular, the present invention relates to a method of treating bacterial infection in a patient suffering from cirrhosis comprising administering to the patient a therapeutically effective amount of a TLR7 and/or TLR8 agonist.

11 Claims, 11 Drawing Sheets

Figure 1A:
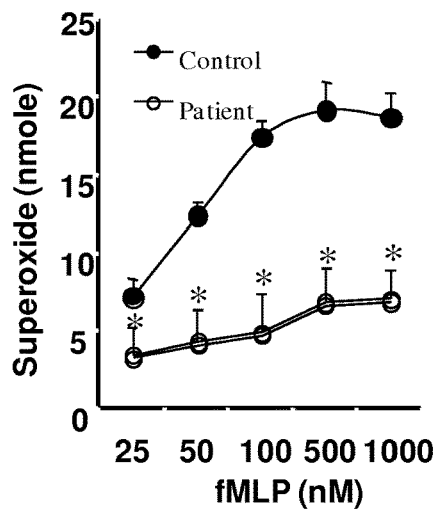

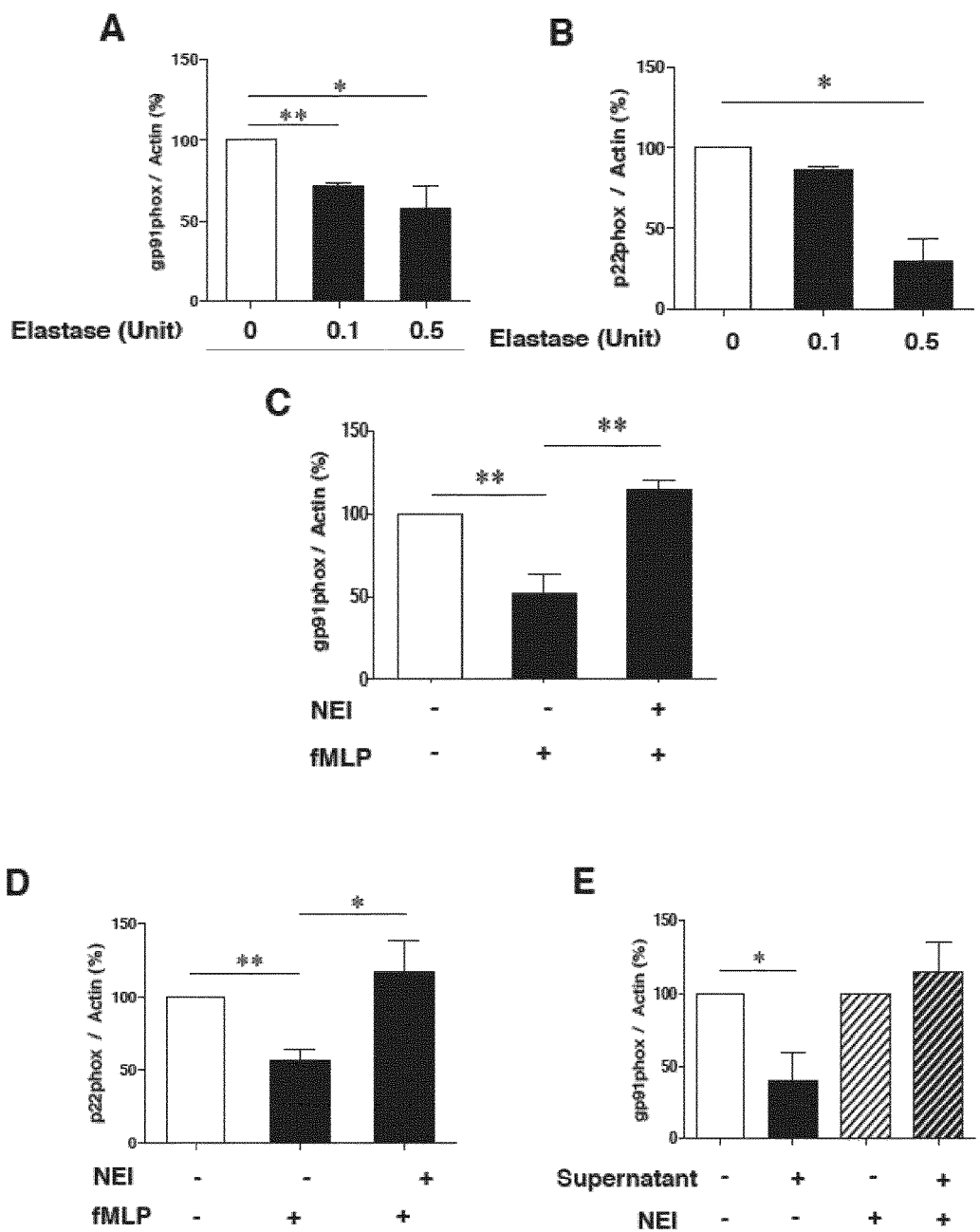
Figure 8 A-E

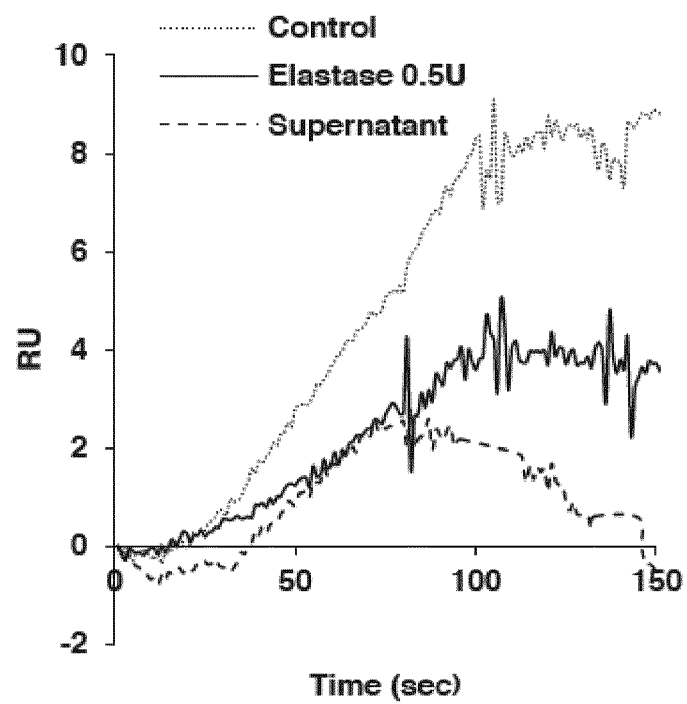
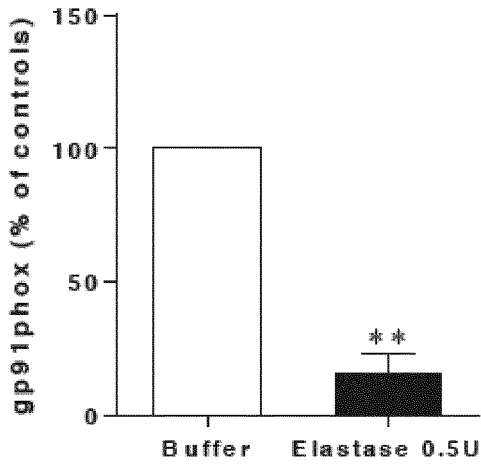
Figure 8 F and G

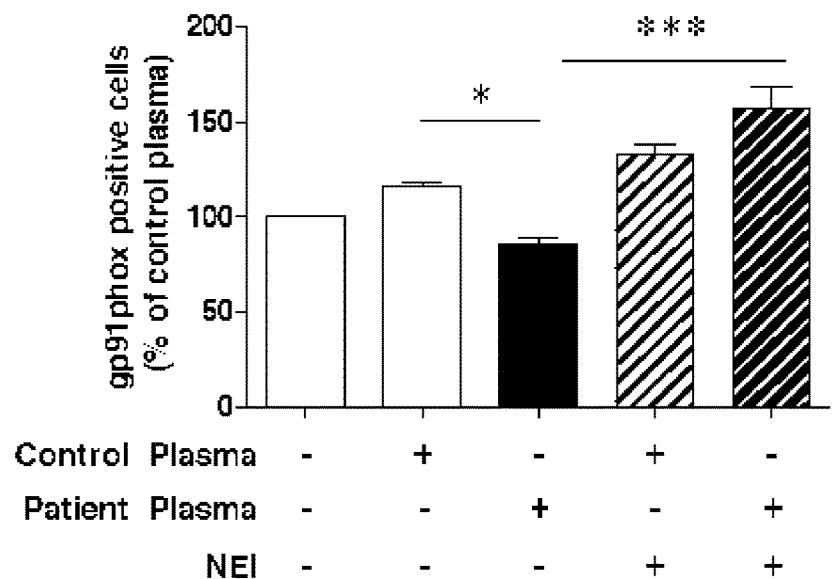
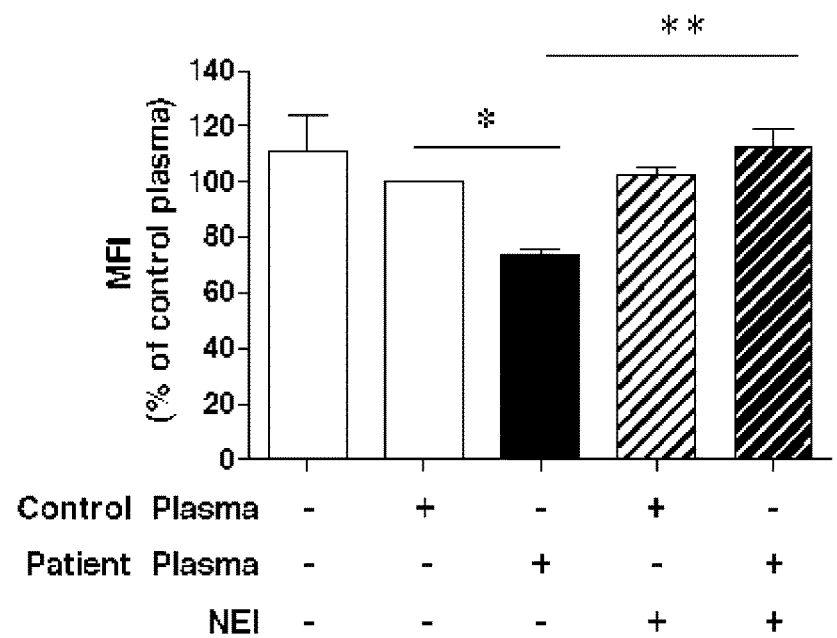
Figure 9 A and B

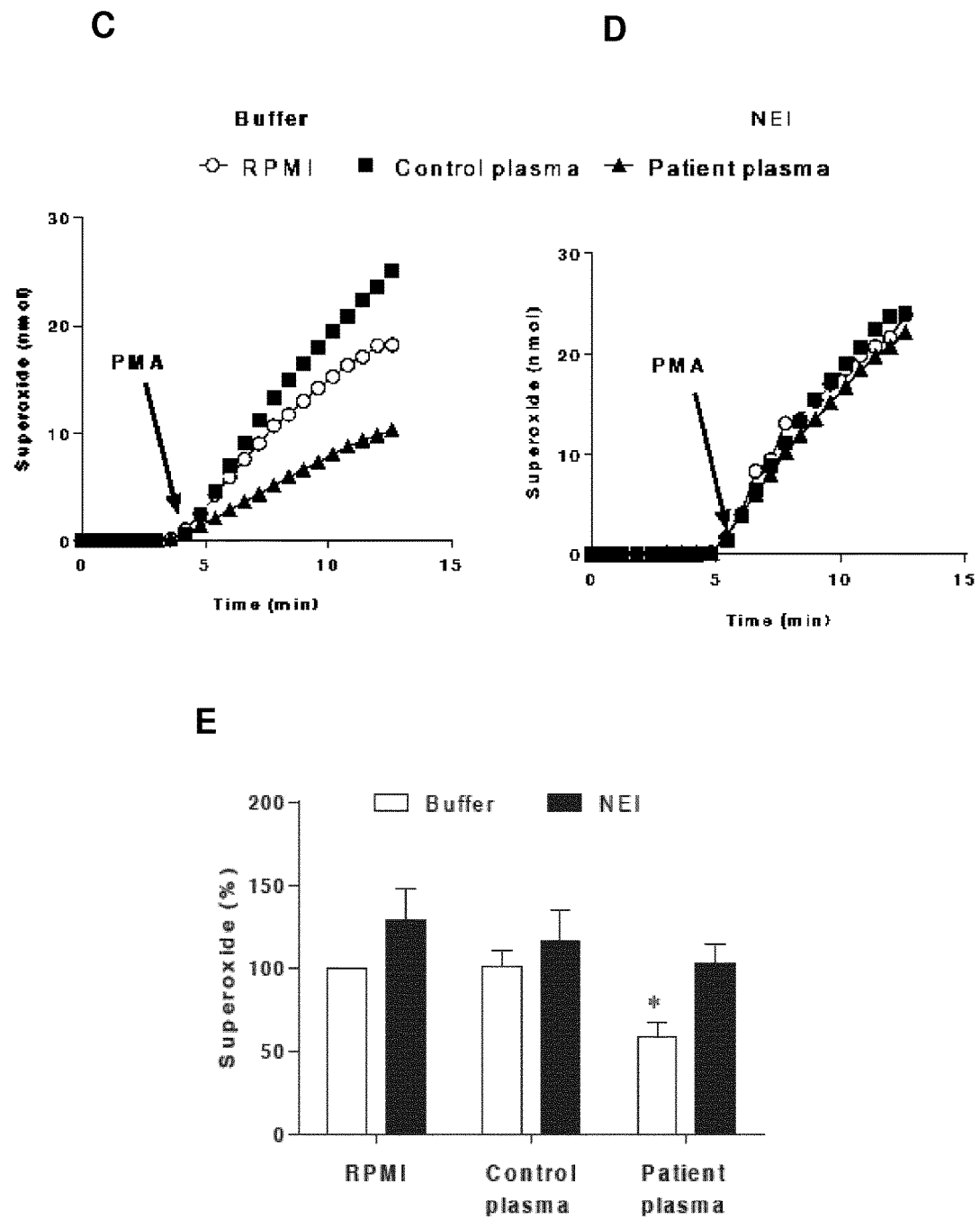
Figure 9 C, D and E

METHODS AND PHARMACEUTICAL COMPOSITIONS FOR THE TREATMENT OF BACTERIAL INFECTIONS IN PATIENTS SUFFERING FROM CIRRHOSIS

FIELD OF THE INVENTION

The present invention relates to methods and pharmaceutical compositions for the treatment of bacterial infections in patients suffering from cirrhosis.

BACKGROUND OF THE INVENTION

Cirrhosis is a chronic disease of the liver whose prevalence will dramatically increase during the next decade. Cirrhosis can result from a number of chronic liver diseases such as alcoholic liver disease, chronic viral hepatitis, non-alcoholic steatohepatitis, autoimmune diseases of the liver (primary biliary cirrhosis, primary sclerosing cholangitis, and autoimmune hepatitis). Cirrhosis progresses over several years. The occurrence of complications indicates the transition to the phase called "decompensated" (approximately 100,000 patients per year in France); These complications include ascites (30,000 patients per year in France), gastrointestinal bleeding (10,000 episodes/year in France), renal failure and bacterial infections which is very common and often due to the translocation of Gram-negative intestinal bacteria.

Reactive oxygen species (ROS) produced by polymorphonuclear leukocytes (PMNs), monocytes or macrophages, termed respiratory burst (RB) or oxidative stress (OS), play a key role in antimicrobial host-defense systems. The enzyme responsible for the phagocyte RB, nicotinamide adenine dinucleotide phosphate (NADPH) oxidase 2 (NOX2), is a membrane multiprotein complex whose activation requires the phosphorylation and membrane translocation of cytosolic components, among which p47phox (phox: phagocyte oxidase) plays an important role. A deficient production of ROS promotes patients' susceptibility to microbial infections. Cirrhosis is a typical example in which inappropriate ROS production induces both tissue damage and patient susceptibility to infections. A common complication of cirrhosis is indeed the development of sepsis, a major cause of death, which is associated with impaired PMN RB, microbicidal activity, and phagocytosis. It was previously shown that neutrophils from patients with advanced alcoholic cirrhosis exhibited a severe deficient production of superoxide induced by the bacterial-derived peptide f-Met-Leu-Phe (fMLP) which was associated with impaired intracellular signaling (Rolas L et al, Hepatology, 2013). More particularly, it was recently disclosed that patient neutrophils were also deficient in Gp91phox expression determined by western-blot analyses (Rolas et al, 1$^{st}$ Meeting of the Neutrophil Club, Apr. 10, 2015, Paris). These data may explain in part the increased susceptibility of patients to bacterial infections and thus do not render credible use of TLR7/8 agonists for the treatment of bacterial infections in patients suffering from cirrhosis despite the fact that such compounds induce hyperactivation of the NADPH oxidase by stimulating the phosphorylation of p47phox on selective sites in healthy human neutrophils (Makni-Maalej et al. J. Immunol. 2012).

SUMMARY OF THE INVENTION

The present invention relates to methods and pharmaceutical compositions for the treatment of bacterial infections in patients suffering from cirrhosis. In particular, the present invention is defined by the claims.

DETAILED DESCRIPTION OF THE INVENTION

The inventors surprisingly show that treatment of patient neutrophils with a cell-permeable agonist of Toll-like receptors 7/8 (TLR7/8) increased Gp91phox mRNA level and restored the expression of the enzyme. More surprisingly, the inventors demonstrate that ROS production induced by said compounds is raised to a level similar of that of neutrophils from healthy donor. Accordingly, despite the observations that TLR7/8 agonists were shown to induce hyperactivation of the NADPH oxidase in human neutrophils (Makni-Maalej et al., J. Immunol. 2012), the suppressing effects observed with said compounds in neutrophils of patients suffering from cirrhosis could not obviously be flowed from the prior art especially in the context where the expression of the targeted enzyme was disclosed to be deficient (Rolas et al, 1$^{st}$ Meeting of the Neutrophil Club, Apr. 10, 2015, Paris).

The inventors also demonstrated that NOX2 depletion by proteolysis occurred in healthy neutrophils treated with elastase, or stimulated with the formylpeptide fMet-Leu-Phe, in an elastase-dependent manner. Moreover, plasma from patients but not control decreased NOX2 expression and activity of neutrophils in an elastase-dependent manner. NOX2 is extensively degraded by extracellular elastase and its deficient synthesis pathways in neutrophils from cirrhotic patients contributes to depletion, which may increase patients' susceptibility to infections.

Accordingly, a first object of the present invention relates to a method of treating bacterial infection in a patient suffering from cirrhosis comprising administering to the patient a therapeutically effective amount of a TLR7 and/or TLR8 agonist.

According to the present invention, patients suffering from cirrhosis typically include patients with alcoholic liver cirrhosis or viral cirrhosis or metabolic. Cirrhosis can result from a number of chronic liver diseases such as alcoholic liver disease, chronic viral hepatitis, non-alcoholic steatohepatitis, autoimmune diseases of the liver (primary biliary cirrhosis, primary sclerosing cholangitis, and autoimmune hepatitis). Patients with liver cirrhosis preferably at the stage of onset or development of decompensated cirrhosis are particularly concerned by the method of the present invention.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In some embodiments, the method of the present invention is particularly suitable for the treatment of bacterial peritonitis in a patient suffering from cirrhosis.

As used herein the term "bacterial peritonitis" has its general meaning in the art and refers to an inflammation of the peritoneal membrane caused by a bacterial infection. Bacterial peritonitis can be classified as primary, secondary, or tertiary. In primary peritonitis (also called spontaneous bacterial peritonitis), the source of infection does not arise from the gastrointestinal tract, and there is no identifiable anatomical derangement of the intra-abdominal viscera. Primary peritonitis is mostly caused by a chronic liver disease, such as cirrhosis. In contrast, secondary peritonitis is due to an infection of the abdominal viscera, and may arise as a consequence of perforation, ischemic necrosis, or penetrating injury. Tertiary peritonitis is defined as peritonitis that persists or recurs after more than one failed source control procedure, and is highly frequent in patients requiring intensive care unit admission for severe abdominal infections.

As used herein, the expressions "agonist of TLR7" and "agonist of TLR8" refer to compounds which bind to and activate TLR7 or TLR8 respectively. The terms "activation" and "stimulation" are used indifferently. "TLR7 and/or TLR8 agonist" or "TLR7/8 agonist" refers to a molecule that is an agonist of TLR7 only, TLR8 only or both TLR7 and TLR8.

TLR7 and/or TLR8 agonists are well known in the art (Waleed M Hussein, Tzu-Yu Liu, Mariusz Skwarczynski, Istvan Toth. Toll-like receptor agonists: a patent review (2011-2013) Expert Opinion on Therapeutic Patents April 2014, Vol. 24, No. 4, Pages 453-470: 453-470). Moreover, methods for identifying agonists of TRL7 or agonists of TLR8 are well known in the art and are described for example in document WO2004/075865 (3M Innovative Properties Company).

Natural agonists of TLR7 and TLR8 have been identified as guanosine- and uridine-rich ssRNA (Diebold, Science 2004, Heil Science, 2004).

Typically, TLR7 agonists include, but are not limited to: imidazoquinoline-like molecules, imiquimod, resiquimod, gardiquimod, S-27609; and guanosine analogues such as loxoribine (7-allyl-7,8-dihydro-8-oxo-guanosine), 7-Thia-8-oxoguanosine and 7-deazaguanosine, UC-1V150, ANA975 (Anadys Pharmaceuticals), SM-360320 (Sumimoto), 3M-01 and 3M-03 (3M Pharmaceuticals) (see for example Gorden et al., J Immunology, 2005; Schön, Oncogene, 2008; Wu et al., PNAS 2007). TLR7 agonists include imidazoquinoline compounds; guanosine analogs; pyrimidinone compounds such as bropirimine and bropirimine analogs; and the like. Imidazoquinoline compounds that function as TLR7 ligands include, but are not limited to, imiquimod, (also known as Aldara, R-837, S-26308), and R-848 (also known as resiquimod, S-28463; having the chemical structure: 4-amino-2-ethoxymethyl-α,α-dimethyl-1H-imidazol[4,5-c]quinoline-1-ethanol). Suitable imidazoquinoline agents include imidazoquinoline amines, imidazopyridine amines, 6,7-fused cycloalkylimidazopyridine amines, and 1,2 bridged imidazoquinoline amines. These compounds have been described in U.S. Pat. Nos. 4,689,338, 4,929,624, 5,238,944, 5,266,575, 5,268,376, 5,346,905, 5,352,784, 5,389,640, 5,395,937, 5,494,916, 5,482,936, 5,525,612, 6,039,969 and 6,110,929. Particular species of imidazoquinoline agents that are suitable for use in a subject method include R-848 (S-28463); 4-amino-2ethoxymethyl-α,α-dimethyl-1H-imidazo[4,5-c]quinoline-s-i-ethanol; and 1-(2-methylpropyl)-1H-imidazo[4,5-c]quinolin-4-amine (R-837 or Imiquimod). Also suitable for use is the compound 4-amino-2-(ethoxymethyl)-α,α-dimethyl-6,7,8,9-tetrahydro-1H-imidazo[4,5-c]quinoline-1-ethanol hydrate (see, e.g., BM-003 in Gorden et al. (2005). Guanosine analogs that function as TLR7 ligands include certain C8-substituted and N7,C8-disubstituted guanine ribonucleotides and deoxyribonucleotides, including, but not limited to, Loxoribine (7-allyl-8-oxoguanosine), 7-thia-8-oxo-guanosine (TOG), 7-deazaguanosine, and 7-deazadeoxyguanosine (Lee et ah, 2003). Bropirimine (PNU-54461), a 5-halo-6-phenyl-pyrimidinone, and bropirimine analogs are described in the literature and are also suitable for use. See, e.g., Vroegop et al. (1999). Additional examples of suitable C8-substituted guanosines include but are not limited to 8-mercaptoguanosine, 8-bromoguanosine, 8-methylguanosine, 8-oxo-7,8-dihydroguanosine, C8-arylamino-2'-deoxyguanosine, C8-propynyl-guanosine, C8- and N7-substituted guanine ribonucleosides such as 7-allyl-8-oxoguanosine (loxoribine) and 7-methyl-8-oxoguanosine, 8-aminoguanosine, 8-hydroxy-2'-deoxyguanosine, and 8-hydroxyguanosine. TLR7-selective agonists also include those shown in U.S. Patent Publication 2004/0171086. Additional suitable TLR7 agonists include, but are not limited to, 2-(ethoxymethyl)-1-(2-methylpropyl)-1H-imidazo[4,5-c]quinolin-4-amine (U.S. Pat. No. 5,389,640); 2-methyl-1-[2-(3-pyridin-3-ylpropoxy)ethyl]-1H-imidazo[4,5-c]quinolin-4-amine (WO 02/46193); N-(2-{2-[4-amino-2-(2-methoxyethyl)-1H-imidazo[4,5-c]quinolin-1-yl]ethoxy} ethyl-ethylN-methylcyclohexanecarboxamide (U.S. Patent Publication 2004/0171086); 1-[2-(benzyloxy)ethyl]-2-methyl-1H-imidazo[4,5-c]quinolin-4-amine (WO 02/46189); N-{8-[4-amino-2-(2-methyoxyethyl)-1H-imidazo[4,5-c]quinolin-1-yl]octyl}-N-phenylurea (U.S. Patent Publication 2004/0171086 (IRM5)); 2-butyl-1-[5-(methylsulfonyl)pentyl]-1H-imidazo[4,5-c]quinolin-4-amine (WO 02/46192); N-{3-[4-amino-2-(2-methoxyethyl)-1H-imidazo[4,5-c]quinolin-1-yl]propyl}-4-methylbenzenesulfonamide (U.S. Pat. No. 6,331,539); and N-[4-(4-amino-2-ethyl-1H-imidazo[4,5-c]quinolin-1-yl)butyl]cyclohexanecarboxamidecarboxamide (U.S. Patent Publication 2004/0171086 (IRM8)). Also suitable for use is the TLR7-selective agonist N-[4-(4-amino-2-ethyl-1H-imidazo[4,5-c]quinolin-1-yl)butyl-]methanesulfon-amide.

For example, TLR8 agonists include, but are not limited to, the compounds shown in U.S. Patent Publication No. 2004/0171086 that include N-{4-[4-amino-2-(2-methoxyethyl)-1H-imidazo[4,5-c]quinolin-1-yl]butyl}quinolin-3-carboxamide, N-{4-[4-amino-2-(2-methoxyethyl)-1H-imidazo[4,5-c]quinolin-1-yl]butyl}quinoxoline-2-carboxamide, and N-[4-(4-amino-2-propyl-1H-imidazo[4,5-c]quinolin-1-yl)butyl]morpholine-4-carboxamide. Other suitable TLR8-selective agonists include, but are not limited to, 2-propylthiazolo[4,5-c]quinolin-4-amine (U.S. Pat. No. 6,110,929); N1-[2-(4-amino-2-butyl-1H-imidazo[4,5-c][1,5]naphthyridin-1-yl)ethyl]-2-amino-4-methylpentanamide (U.S. Pat. No. 6,194,425); N1-[4-(4-amino-1H-imidazo[4,5-c]quinolin-1-yl)butyl]-2-phenoxy-benzamide (U.S. Pat. No. 6,451,810); N1-[2-(4-amino-2-butyl-1H-imidazo[4,5-c]quinolin-1-yl)ethyl]-1-propanesulfonamide (U.S. Pat. No. 6,331,539); N-{2-[2-(4-amino-2-ethyl-1H-imidazo[4,5-c]quinolin-1-yl)ethyoxy]ethyl}-N'-phenylurea (U.S. Patent Publication 2004/0171086); 1-{4-[3,5-dichlorophenyl)thio]butyl}-2-ethyl-1H-imidazo[4,5-c]quinolin-4-amine (U.S. Patent Publication 2004/0171086); N-{2-[4-amino-2-(ethoxymethyl)-1H-imidazo[4,5-c]quinolin-1-yl]ethyl}-N'-(3-cyanophenyl)urea (WO 00/76518 and U.S. Patent Publication No. 2004/0171086); and 4-amino-α,α-dimethyl-2-methoxyethyl-1H-imidazo[4,5-c]quinoline-1-ethanol (U.S. Pat. No. 5,389,640). Included for use as TLR8-selective agonists are the compounds in U.S. Patent Publication No. 2004/0171086. Also suitable for use is the compound 2-propylthiazolo-4,5-c]quinolin-4-amine.

Specific examples of TLR7/8 agonists of the present invention include:

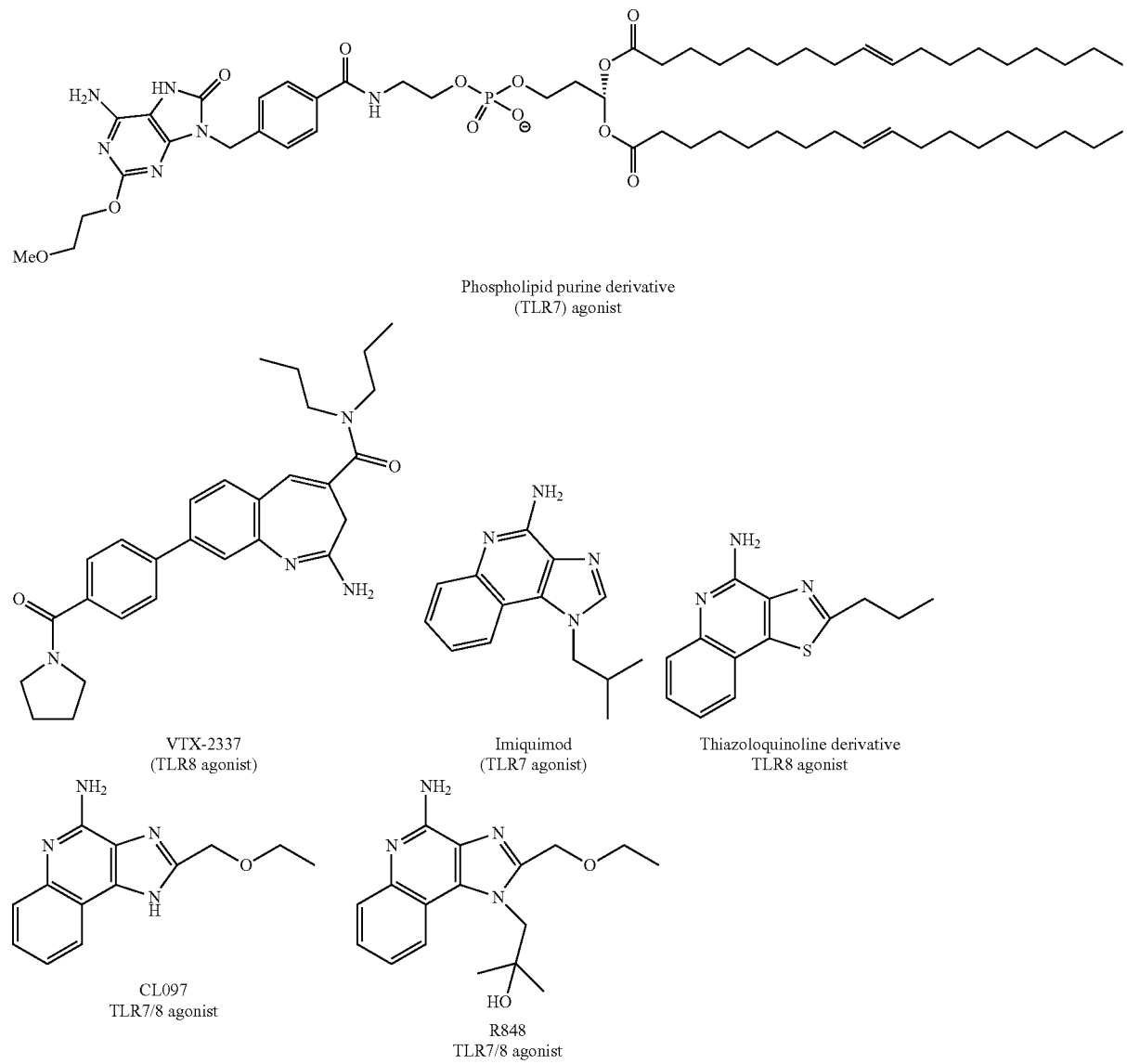

In some embodiments, the TLR7/8 agonist of the present invention is R848. By "R848" is meant an imidazoquinoline compound with the structure above described.

In some embodiments, the TLR7/8 agonist of the present invention is incorporated in a particle appropriate for ingestion by neutrophils. Accordingly, the dimensions of the particle (e.g. diameter) are selected to promote phagocytosis of the particles by neutrophils. In some embodiments, the present invention provides a population of particles wherein the TLR7/8 agonist of the present invention is incorporated and, wherein at least 50% of the particles have a size appropriate for ingestion by neutrophils. In some embodiments, the desired size ranges within ±10%, ±20%, ±30%, ±40%, or ±50% of a given value. The value may be, e.g. 20 nm, 100 nm, 500 nm, 1, 5, 10, 20, 50 microns, etc. The particles in any of these embodiments can result from any composition. Typically, the particles comprise denatured proteins (e.g. human serum albumin (Benacerraf et al., 1957 Brit. J. Exp. Path, 38:35)), insoluble materials (e.g. carbon black, silica, silicon dioxide, polystyrene, latex), metal oxides (e.g. titanium oxides, iron oxides), and India ink (i.e., suspension of colloidal carbon particles) (described in Reichard and Filkins, 1984, The Reticuloendothelial System; A Comprehensive Treatise, pp. 73-101 (Plenum Press), and references therein), hydrogels, (for example as described in US Patent Publication No. 20050191361), sepharose or agarose beads or microparticles. In some embodiments, the particles are formed from materials that are biodegradable and non-toxic (e.g. a poly(α-hydroxy acid) such as poly(lactide-co-glycolide), a polyhydroxybutyric acid, a polyorthoester, a polyanhydride, a polycaprolactone, etc.). The particles of the present invention may comprise red blood cells (RBCs) that have been purged of their cytoplasm, known as 'Ghost' RBCs, bacteria (as bacteria are cleared by the RES; see, e.g. Benacerraf and Miescher, 1960, Ann NY Acad Sci, 88:184-195), cell fragments, liposomes, bacteriophages, bacteriophage fragments, and viral capsids devoid of the viral nucleic acids (e.g. hepatitis B virus surface antigen particles), etc.

As used herein, the term "effective amount" refers to a quantity sufficient to achieve a therapeutic effect (e.g. treating bacterial infection). In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. In some embodiments, an effective amount of TLR7/8 agonist for achieving a therapeutic or prophylactic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In some embodiments, a single dosage of peptide ranges from 0.1-10,000 micrograms per kg body weight. In some embodiments, aromatic-cationic peptide concentrations in a carrier range from 0.2 to 2000 micrograms per delivered milliliter.

Typically, the TLR7/8 agonist of the present invention is combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The pharmaceutical composition is compatible with any route of administration (oral, injection, . . . ). For example, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Sterile injectable solutions are prepared by incorporating the TLR7 and/or TLR8 agonist of the present invention in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In some embodiments, the TLR7/8 agonist of the present invention is administered concomitantly with an antibiotic. In some embodiments, the antibiotic is selected from the group consisting of aminoglycosides, beta lactams, quinolones or fluoroquinolones, macrolides, sulfonamides, sulfamethaxozoles, tetracyclines, streptogramins, oxazolidinones (such as linezolid), rifamycins, glycopeptides, polymixins, lipo-peptide antibiotics. Typically beta lactames include 2-(3-alanyl)clavam, 2-hydroxymethylclavam, 7-methoxycephalosporin, epi-thienamycin, acetyl-thienamycin, amoxicillin, apalcillin, aspoxicillin, azidocillin, azlocillin, aztreonam, bacampicillin, blapenem, carbenicillin, carfecillin, carindacillin, carpetimycin A and B, cefacetril, cefaclor, cefadroxil, cefalexin, cefaloglycin, cefaloridine, cefalotin, cefamandole, cefapirin, cefatrizine, cefazedone, cefazolin, cefbuperazone, cefcapene, cefdinir, cefditoren, cefepime, cefetamet, cefixime, cefinenoxime, cefinetazole, cefiiiinox, cefmolexin, cefodizime, cefonicid, cefoperazone, ceforamide, cefoselis, cefotaxime, cefotetan, cefotiam, cefoxitin, cefozopran, cefpiramide, cefpirome, cefpodoxime, cefprozil, cefquinome, cefradine, cefroxadine, cefsulodin, ceftazidime, cefteram, ceftezole, ceftibuten, ceftizoxime, ceftriaxone, cefuroxime, cephalosporin C, cephamycin A, cephamycin C, cephalothin, chitinovorin A, chitinovorin B, chitinovorin C, ciclacillin, clometocillin, cloxacillin, cycloserine, deoxy pluracidomycin B and C, dicloxacillin, dihydro pluracidomycin C, epicillin, epithienamycin D, E, and F, ertapenem, faropenem, flomoxef, flucloxacillin, hetacillin, imipenem, lenampicillin, loracarbef, mecillinam, meropenem, metampicillin, meticillin (also referred to as methicillin), mezlocillin, moxalactam, nafcillin, northienamycin, oxacillin, panipenem, penamecillin, penicillin G, N, and V, phenethicillin, piperacillin, povampicillin, pivcefalexin, povmecillinam, pivmecillinam, pluracidomycin B, C, and D, propicillin, sarmoxicillin, sulbactam, sultamicillin, talampicillin, temocillin, terconazole, thienamycin, andticarcillin. Typically, quinolones include nalidixic acid, cinoxacin, oxolinic acid, flumequine, pipemidic acid, rosoxacin, norfloxacin, lomefloxacin, ofloxacin, enrofloxacin, ciprofloxacin, enoxacin, amifloxacin, fleroxacin, gatifloxacin, gemifloxacin, clinafloxacin, sitafloxacin, pefloxacin, rufloxacin, sparfloxacin, temafloxacin, tosufloxacin, grepafloxacin, levofloxacin, moxifloxacin, and trovafloxacin.

In a further aspect, the method of the invention comprises administering to the patient with a therapeutically effective amount of the TLR7 and/or TLR8 agonist according to the invention in combination with an elastase inhibitor.

As used herein, the term "elastase" has its general meaning in the art and refers to the neutrophil elastase, a serine protease produced by neutrophils (Distelhorst et al., 1987; Edwards and Bernstein, 1994; Groutas et al., 2011; Aikawa and Kawasaki, 2014).

A used herein the term "elastase inhibitor" has its general meaning in the art and refers to any compound able to inhibit elastase activity and selectively blocks or inactivates elastase. As used herein, the term "selectively blocks or inactivates" refers to a compound that preferentially binds to and blocks or inactivates elastase with a greater affinity and potency, respectively, than its interaction with the other sub-types or isoforms of the serine protease family. Compounds that prefer elastase, but that may also block or inactivate other serine protease sub-types, as partial or full inhibitors, are contemplated. The "elastase activity inhibitor" refers to compounds that block elastase interaction with its targets proteins. The term "elastase inhibitor" also refers to a compound that inhibits elastase expression. Typically, an elastase inhibitor compound is a small organic molecule, a polypeptide, an aptamer, an antibody, an intra-antibody, an oligonucleotide or a ribozyme.

Tests and assays for determining whether a compound is an elastase inhibitor are well known by the skilled person in the art such as described in Edwards and Bernstein, 1994; EP 0,643,075; US 2005/0265946.

Elastase inhibitors are well-known in the art as illustrated by Edwards and Bernstein, 1994; Groutas et al., 2011; Aikawa and Kawasaki, 2014; Alam et al., 2012; EP 0,643,075; and US 2005/0265946.

In one embodiment of the invention, elastase inhibitors include but are not limited to neutrophil elastase inhibitor MeOSuc-AAPV-CMK (NEI); sivelestat; elafin; α1-antitrypsin (α1-PI); secretory leucocyte protease inhibitor (SLPI); Depelstat (DX-890); and ONO-6818.

In one embodiment of the invention, elastase inhibitors include but are not limited to peptide-based inhibitors (Non-Mechanism-Based Peptidic Inhibitors, P1 Amino Acid Isostere Inhibitors, Electrophilic Carbonyl Derivatives, Boronic Acids, and Monohalomethyl Ketones); Heterocyclic Inhibitors such as Enzyme-Activated Heterocyclic Inhibitors (Halo Enol Lactones, Ynenol Lactones, Isocoumarins, β-Lactams, Succinimides) and Heterocyclic Acylating Agents (Pyrones, Benzoxazinones and Related Heterocycles, and Benzisothiazo lines); Nonheterocyclic AcylatingiAlkylating Agents (Organophosphorus and Organosulfur Agents, Isocyanates and Ester Acylating Agents) such as described in Edwards and Bernstein, 1994.

In one embodiment of the invention, elastase inhibitors include but are not limited to:

Transition state inhibitors such as:

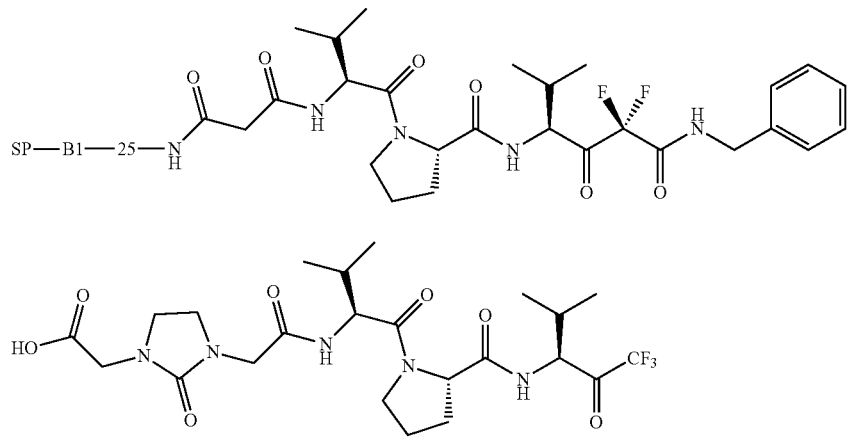

Alternate substrate inhibitors such as:

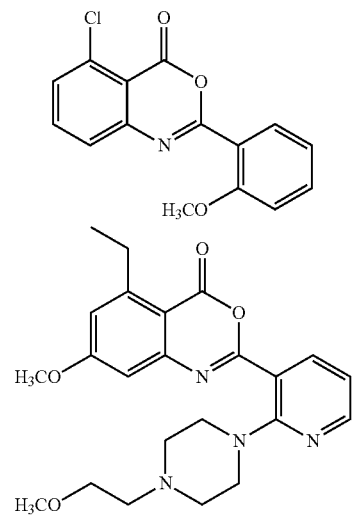

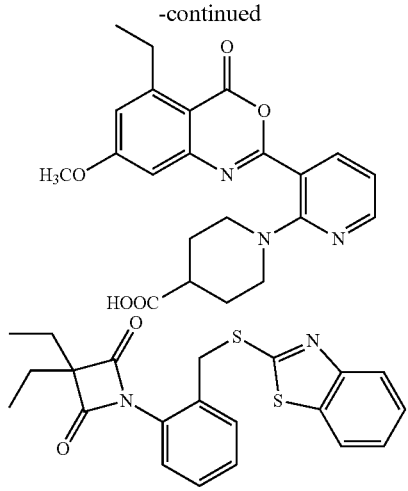
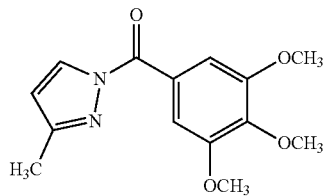
Carbamylating agents; Mechanism-based inhibitors; Reversible competitive inhibitors such as:
1,4-Diarylpyrimidopyridazinyldiones;
4-(4-cyanophenyl)-1-(3-trifluoromethylphenyl)-3,4,6,7-tetrahydro-1H-pyrrolo[3,4-d]pyrimidine-2,5-diones; and compounds described in Groutas et al., 2011 such as:
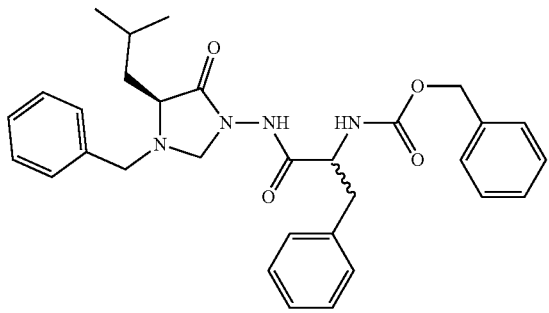
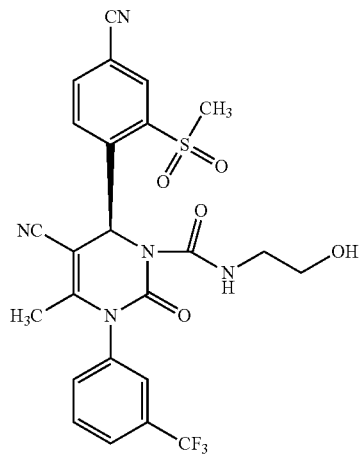
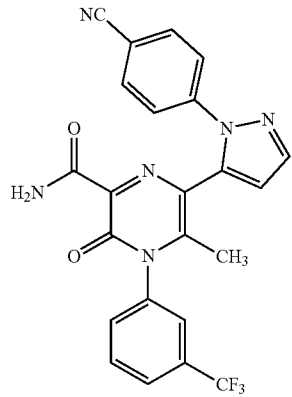

-continued
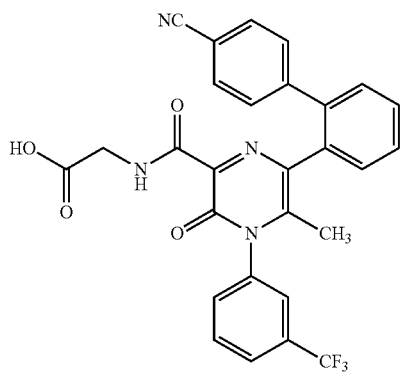
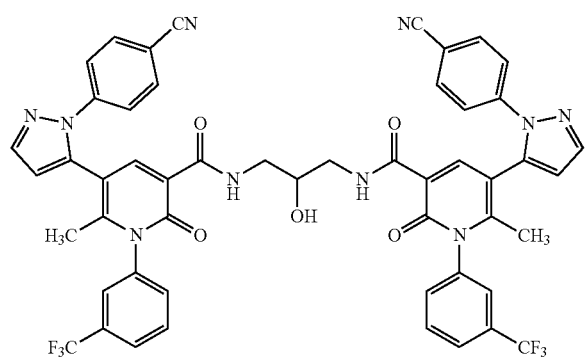
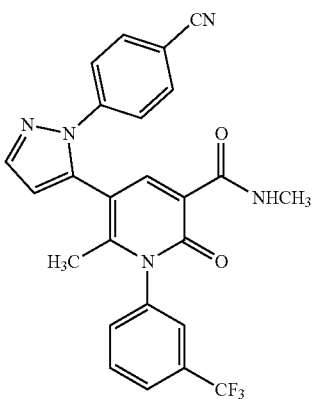
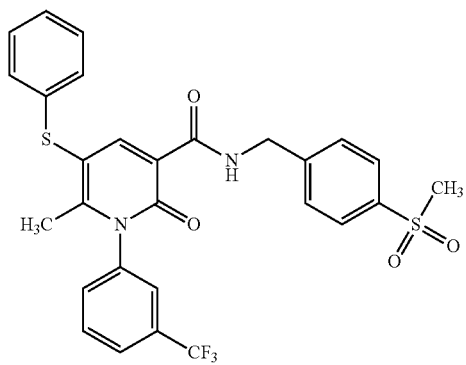

-continued

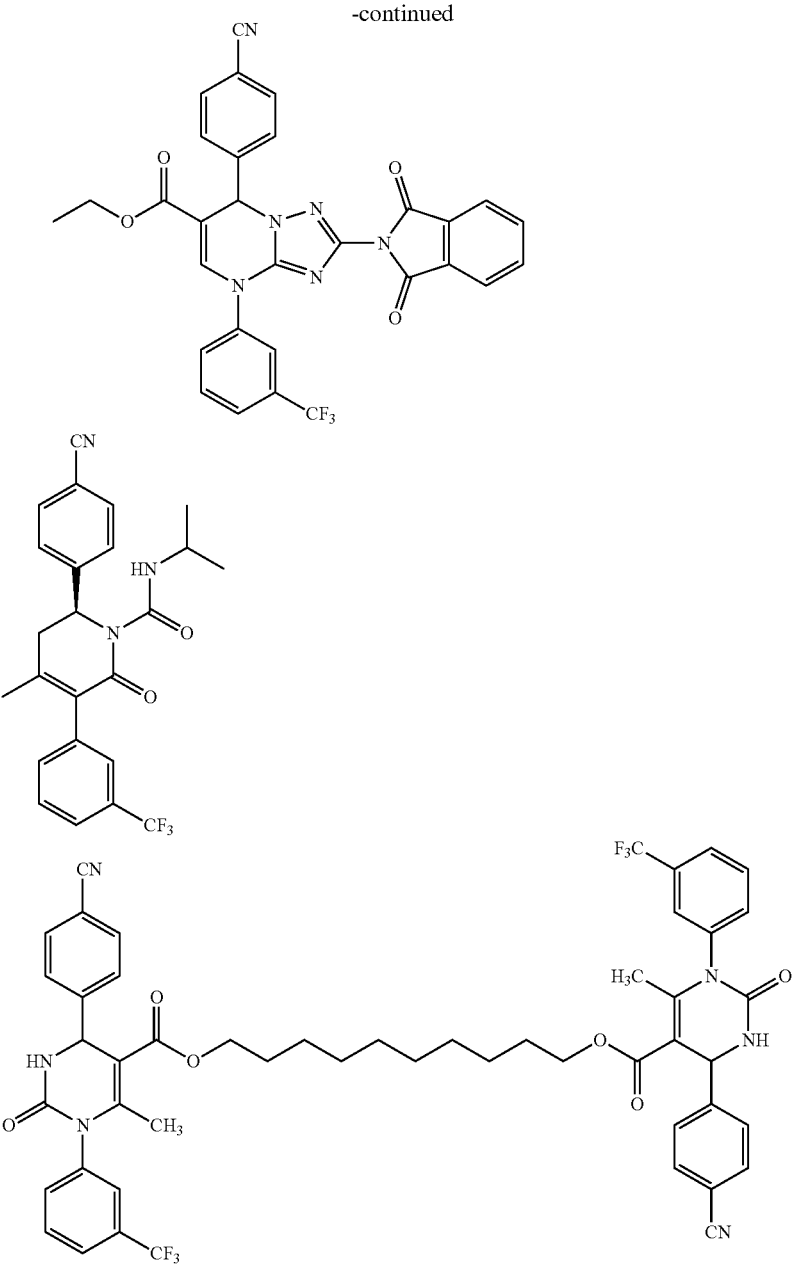

According to the present invention, the TLR7/8 agonist of the invention is administered sequentially or concomitantly with the elastase inhibitor.

The invention will be further illustrated by the following figures and examples. However, these examples and figures should not be interpreted in any way as limiting the scope of the present invention.

FIGURES

Figure 1B:
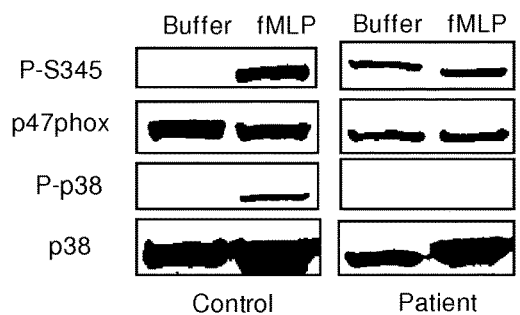
Figure 1C:
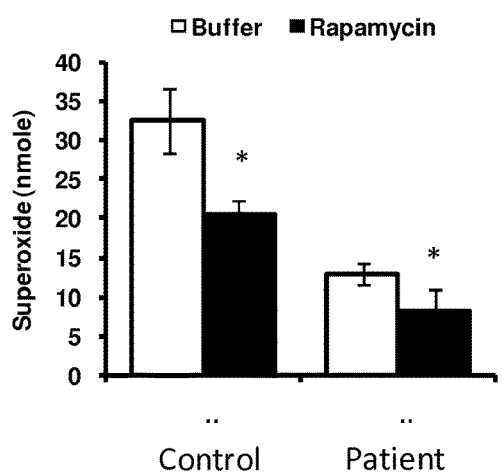

FIG. 1: Neutrophils from patients with advanced alcoholic cirrhosis exhibited impaired fMLP-induced ROS production and signaling. Panel A: PMN from healthy volunteers (control) and cirrhotic patients were stimulated with bacterial—derived peptide fMet-Leu-Phe (fMLP) at various concentrations (25-1000 nM) and the production of superoxide was quantified and expressed in nmole/$10^6$ cells (n=16, *: P<0.05). Panel B: PMN were stimulated with fMLP (1 μM) for 75 sec. The active phosphorylated form of p38 MAPK and p47phox (S345) was detected by western-blot experiments and expressed as percentage of control values obtained with fMLP (n=4). Panel C: PMN ($10^6$ cells/ml) were treated in the absence or presence of 10 nM rapamycin for 15 min before stimulation with fMLP (1 μM). Data represent the mean of superoxide production±SEM (n=8, *: P<0.05) (Data published in Rolas L. et al, *Hepatology* 2013).

Figure 2:
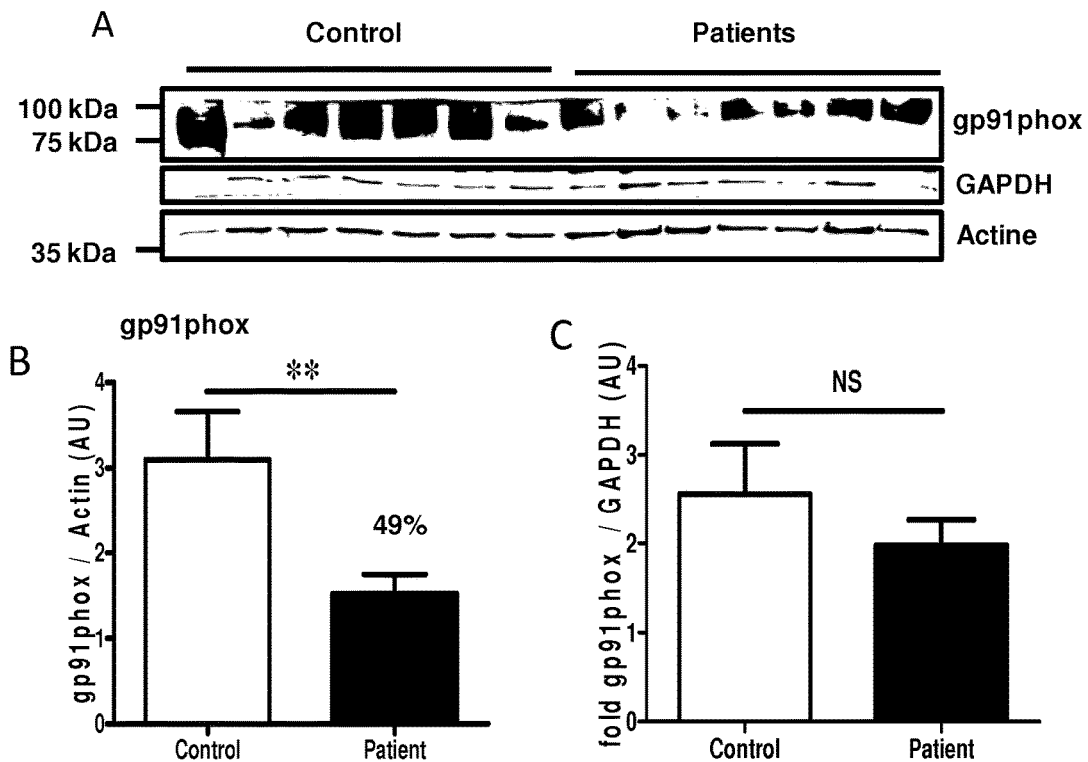

FIG. 2. Deficient expression of the superoxide-generating NADPH oxidase Gp91phox in neutrophils from patients with advanced alcoholic cirrhosis. The expression of Gp91phox of neutrophils from healthy donors (control) and patients with advanced alcohol cirrhosis was determined by western-blot experiments (Panel A), and at the mRNA level (Panel C). Protein expression and mRNA were quantified (Panel B, C) and expressed as percentage±SEM of control values (n=12 in each group, *: P<0.05, Mann-Whitney statistical test).

Figure 3A:
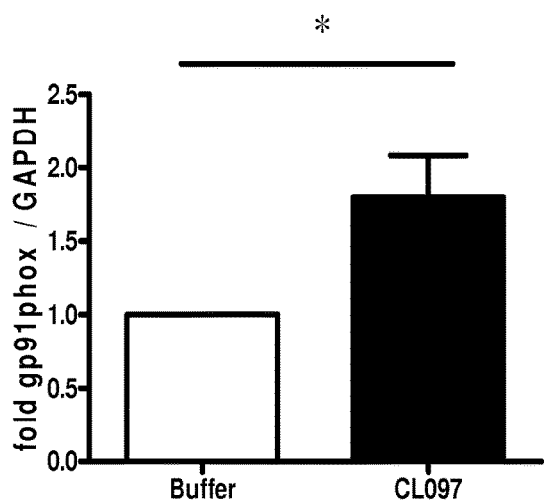

FIG. 3. The TLR7/8 agonist CL097 stimulated Gp91phox RNA production and synthesis in neutrophils from patients with advanced alcohol cirrhosis. Neutrophils from cirrhotic patients were treated in the absence (buffer) or presence of CL097 (2.5 µg/ml) for 30 min at 37° C. and the amount of Gp91phox mRNA was quantified and expressed as percentage of control (Buffer) (Panel A, n=6, *: P<0.05). The expression of Gp91phox was determined by western-blot assays and expressed as percentage±SEM of that of neutrophils of healthy donors (Panel B, n=4, *: P<0.05).

Figure 4:
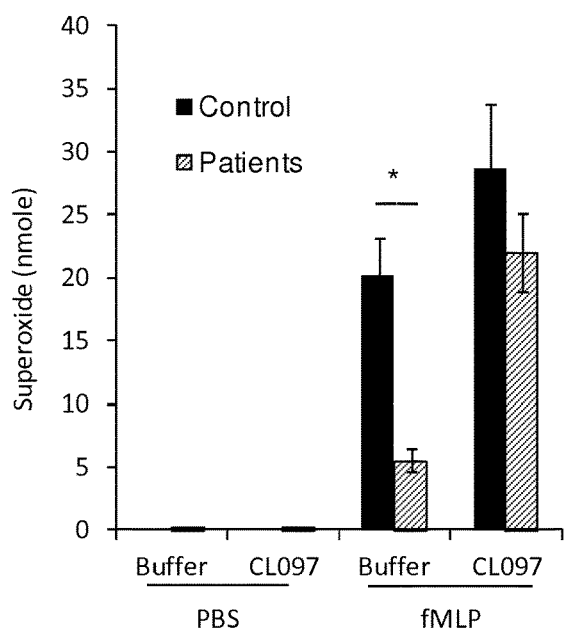

FIG. 4. The TLR7/8 agonist CL097 restored the production of superoxide in neutrophils from patients with advanced alcohol cirrhosis. Neutrophils from healthy donors and patients with advanced alcoholic cirrhosis were treated for 15 min with the TLR7/8 agonist (2.5 µg/ml), then with PBS or 1 µM fMLP. Results represent the mean of superoxide production±SEM expressed in nmole/$10^6$ cells (n=8, *: P <0.05).

Figure 5:
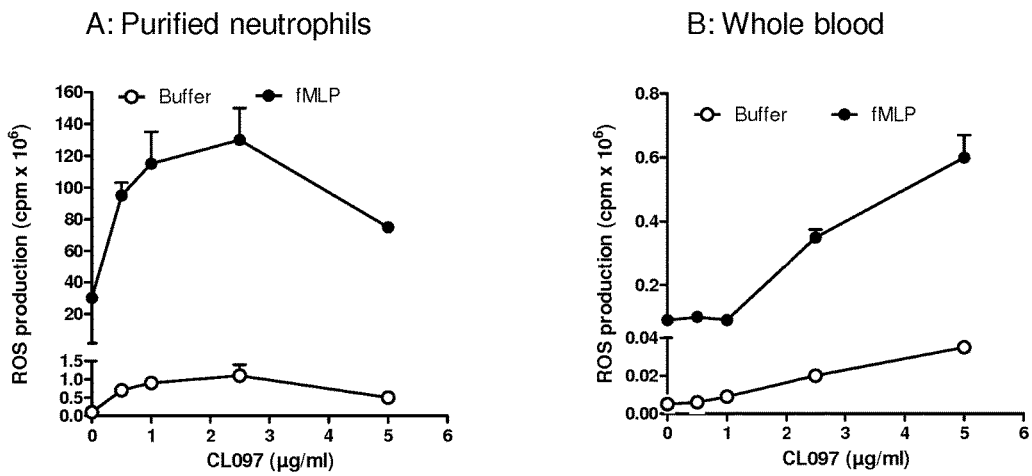

FIG. 5. The TLR7/8 agonist CL097 restored the production of reactive oxygen species by purified neutrophils and in whole blood from patients. ROS production was measured by the highly sensitive luminol-enhanced chemiluminescence assay with purified neutrophils ($0.5 \times 10^6$ cells/450µl Hanks Balanced salt solution, Panel A) and with whole blood (20 µl in 450 µl PBS containing 0.120 mM calcium, Panel B) from patients with advanced alcohol cirrhosis. Cells were treated for 15 min with the TLR7/8 agonist alone (Buffer), then with 1 µM fMLP (Panel A). Results represent the peak of chemiluminescence response expressed in cpm (mean±SEM of 8 experiments).

Figure 6:
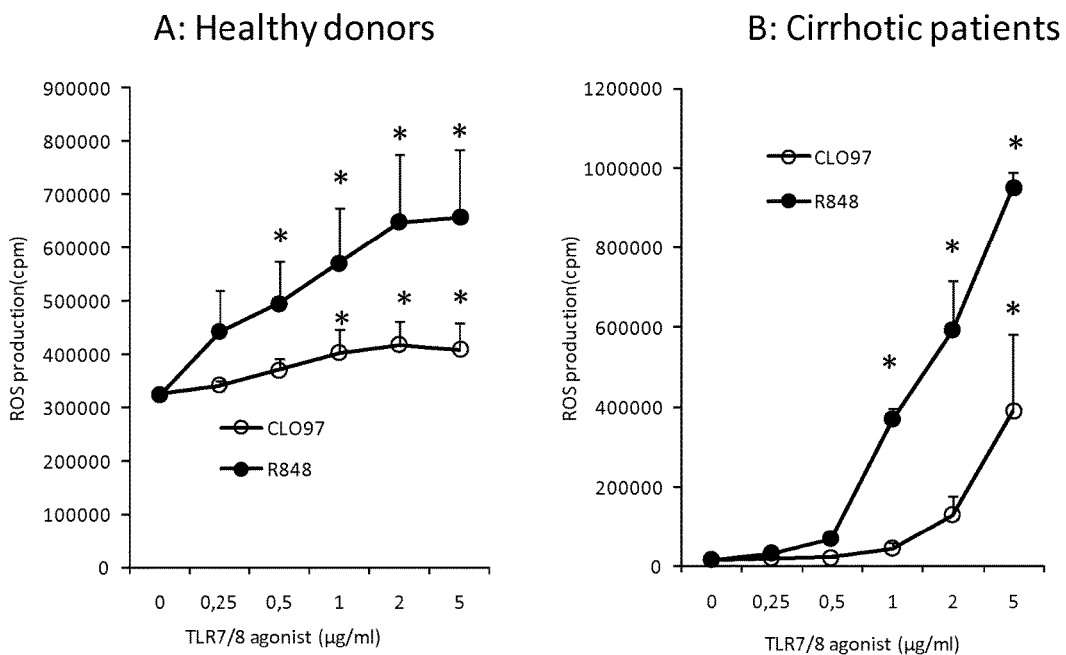

FIG. 6. The TLR7/8 agonist R848 is more potent than CL097 to improve ROS production in whole blood of healthy donors and cirrhotic patients. Whole blood (20 µl) from healthy donors (Panel A) and cirrhotic patients (Panel B) were treated in 450 µL PBS containing 0.120 mM calcium), in the absence (control) and presence of R848 or CL097 (0.25-5 µg/ml) for 15 min. Cells were then stimulated with 1 µM fMLP. Results represent the peak of chemiluminescence response induced by fMLP and are expressed in cpm (mean±SEM of 4-6, *: P<0.05).

Figure 7A:
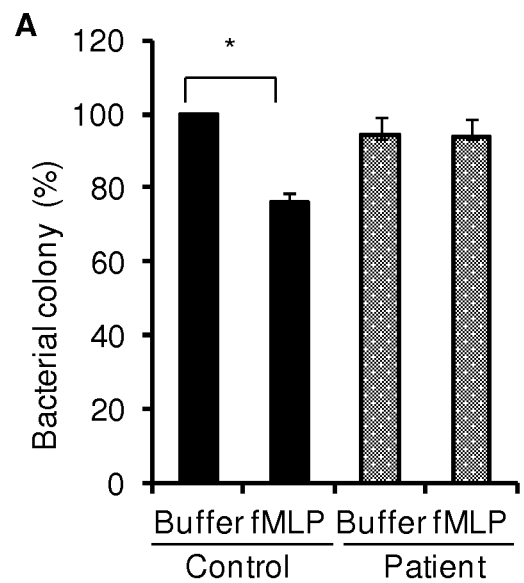
Figure 7B:
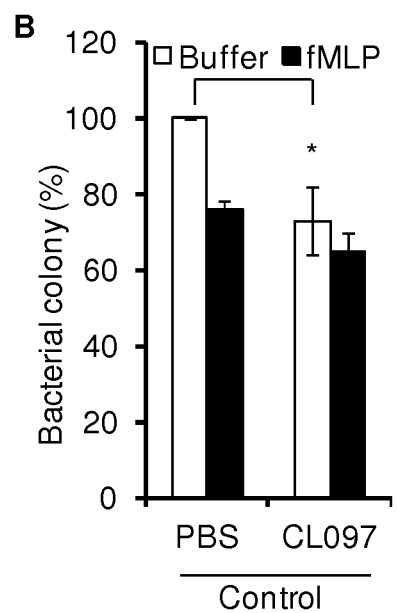
Figure 7C:
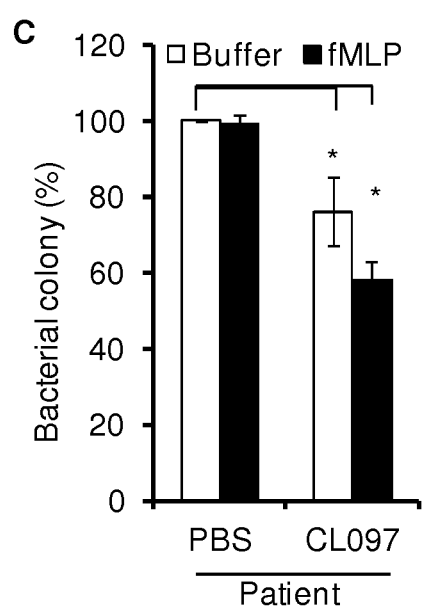

FIG. 7. Impaired bactericidal activity of neutrophils from cirrhotic patients and beneficial effects of the TLR7/8 agonist CL097. (A) Neutrophils from healthy volunteers (Control) and cirrhotic patients were incubated with *E coli* for 5 min, then treated or not (Buffer) with fMLP (1 µM) for 25 min. (B, C): Neutrophils incubated with bacteria were treated without (PBS) and with CL097 (1 µg/ml) for 2 min before stimulation with fMLP for 23 min. Cells were lysed and the number of bacterial colony was determined and expressed as percentage of that of control resting cells (A, n=6), or % of that of resting cells (PBS) in both cell populations (B, C, n=6); *P<0.05 (Data published in Boussif A et al, *J Hepatol*. 2016 64:1041-8. doi: 10.1016/j.jhep.2015.12.005. Epub 2015 Dec. 21).

FIG. 8. Elastase induces the degradation of gp91phox and p22phox in healthy PMN. (A and B) Western-blot analysis and densitometric quantification of gp91phox and p22phox in healthy PMN treated in the absence or presence of elastase at 0.1 and 0.5 units for 1 hour. (C and D) Western-blot analysis densitometric quantification of gp91phox and p21phox in healthy PMN treated in the absence or presence of the elastase inhibitor (NEI) at 100 µM for 15 min before stimulation with fMLP (1 µM) for 45 min. (E) Western-blot analysis densitometric quantification of gp91phox in healthy PMN pretreated in the absence or presence of the elastase inhibitor (NEI) at 100 µM for 15 min before incubation for 45 min with a cell-free degranulation supernatant obtained from fMLP (1 µM, 2 min) stimulated PMN. Blots are representative of 4 experiments and densitometric analyses are cumulative and expressed as percentage of the actin level. A significant difference between mean values±SEM is indicated by *P<0.05, and **P<0.01. (F) Sensorgrams of the PMN specific binding and dissociation to the anti-gp91phox antibody (7D5) coated to the CM3 sensorchip, analysed with the Biacore X100, as a function of time. Three groups of PMN were injected ($10^3$ cells in 150 µl PBS); Control PMN and PMN treated with elastase (0.5 units) or with a cell-free degranulation supernatant. Data are representative of 3 independent experiments are expressed as resonance unit (RU). (G) Flow cytometry quantification of the Gp91phox expression at the surface of PMN treated or not (Control) with 0.5 unit Elastase at 4° C. Data represent the mean fluorescent Index (MFI) expressed as percentage±SEM of control values (n=3)

FIG. 9. Plasma from cirrhotic patients reduces gp91phox expression at the surface of healthy PMN and ROS production in NEI-sensitive manner. PMN were pretreated for 12 H at 37° C. with RPMI (control) or with plasma of healthy volunteers or cirrhotic patients, (25% plasma in 1 ml RPMI containing $5 \times 10^6$ PMN) either in the absence or presence of the elastase inhibitor NEI (100 µM). PMN were labelled with the anti-gp91phox FITC-coupled antibody. (A) Quantification of the number of positive cells labeled with the anti-gp91phox FITC-coupled antibody (7D5) by Flow cytometry, expressed as percentage of control values. (B) The right panel shows the MFI values (mean±SEM) expressed as percentage of control values (n=5 separate experiments). (C, D) Time course production of superoxide induced by PMA by healthy PMN which were pretreated for 12 H in the absence (Buffer/RPMI) or presence of plasma from healthy volunteers and cirrhotic patients, either with or without 100 µM NEI. (E) Production of superoxide expressed as percentage of control values (mean±SEM, n=5). A significant difference between mean values is indicated by *P<0.05, and **P<0.01.

Figure 10:
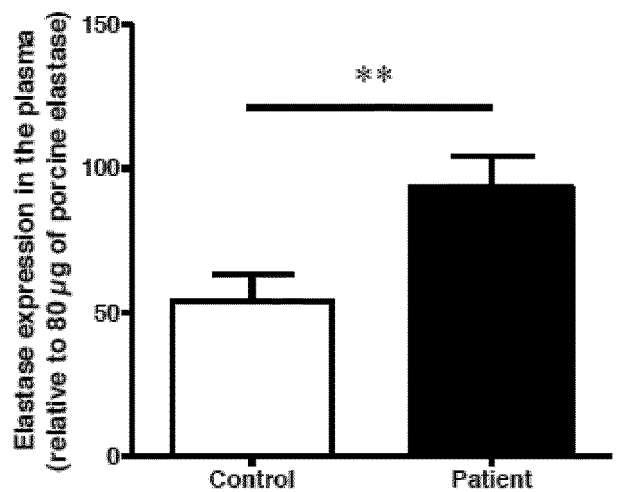

FIG. 10. Plasma from patients with alcohol liver cirrhosis contain greater amount of elastase than controls. Aliquots of 5 µl of plasma (equivalent of 10 µg proteins) were denatured in 450 µl of 1× Laemmli buffer. SDS-PAGE were run with 100 µL of sample. Densitometric analysis and quantification of elastase, and expression relative to 80 µg or porcine elastase which was western-blotted in the same gels, as reference (not shown). Bars represent the mean±SEM obtained with 10 patient's plasma. A significant difference between mean groups of values is indicated by **P<0.01. The absence of p47phox signal indicates that the elastase present in the plasma does not come from of intact or necrotic neutrophils (Data not shown).

Figure 11:
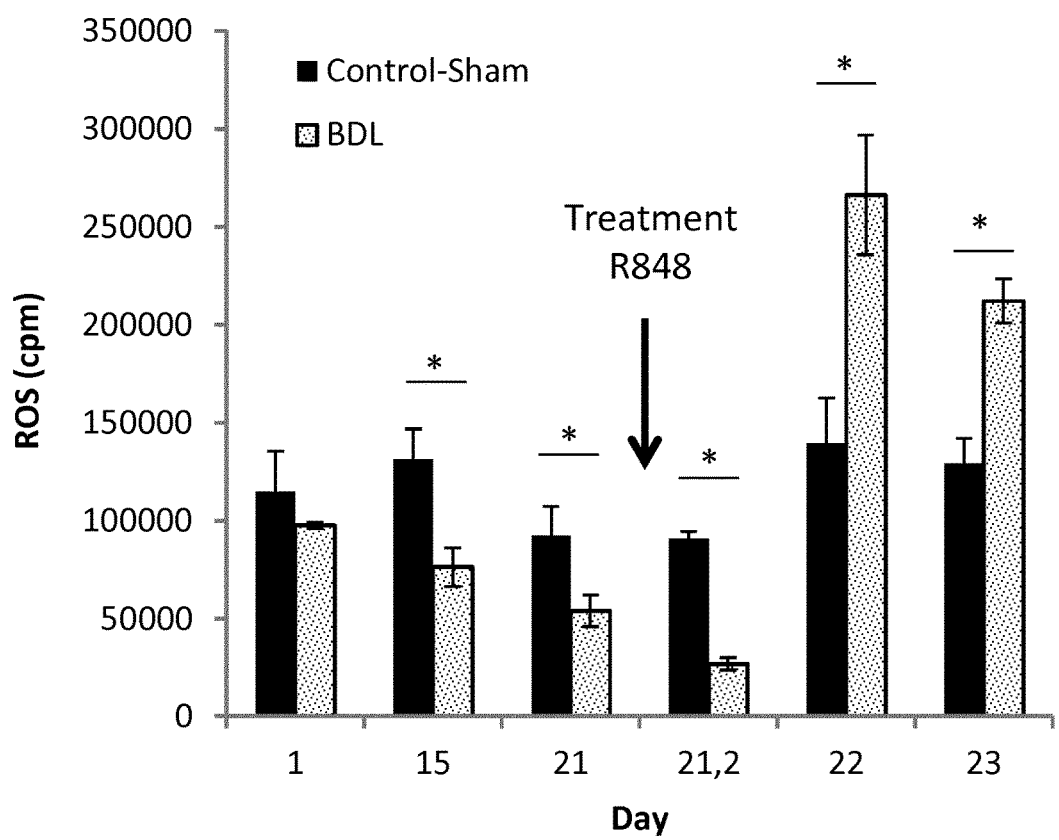

FIG. 11. In vivo treatment of cirrhotic rats by R848 reverses the deficient ROS production in whole blood. The common bile duct with Wistar female rats was ligated (BDL) under general anesthesia (10 mg Avertin, IP) close to the liver hilum immediately below the bifurcation as described previously (Mohammadi et al, Liver Int. 2009, 29(5):692-700). All surgical procedures were performed under sterile conditions. Blood was collected in Eppendorf tubes (approximately 0.5 ml in 10 mM EDTA) with a 1 inch hypodermic needle inserted into the vessel in the mid ventral surface of the tail. White blood cells were counted using a MS9-5V Analyser Counter (Melet Schloesing Laboratories). At day 21, the cirrhotic BDL rats were treated with R848

(2.2 mg/kg) as reported (McCluskie M J et al, *Antiviral Res.* 69:77-85, 2006). Control rats were not treated. The production of reactive oxygen species were measured in whole blood at the indicated day. Briefly, ROS production was continuously recorded in a thermostated bioluminometer (Berthold LB940) using 3 blood volumes (0.9, 1.8 and 3.75 µl) incubated at 37° C. in 0.5 ml Hanks balanced salt solution (HBSS) containing 10 µM luminol. Cells were treated with cytochalasin b (0.25 µg/ml) for 5-10 min then stimulated with the bacterial-derived peptide fMet-Leu-he (fMLP, 1 µM). ROS production represents the peak of chemiluminescence response in whole blood. A typical profil response from representative rats is provided for the indicated day (mean of triplicate determinations±SEM) expressed in cpm per equivalent of 2000 blood PMN. Similar profil responses were obtained with a total of 6 BDL rats and 5 untreated control (sham) rats.

EXAMPLES

Example 1

Utility of TLR7/8 Agonists CL097 and R848 to Restore NADPH Oxidase Activity of Neutrophils of Immuno-Compromised Patients with Advanced Alcoholic Cirrhosis The human phagocyte cytochrome b of NADPH oxidase (Gp91phox) is an important plasma membrane terminal effector of the microbicidal superoxide-generating system. We previously showed that neutrophils from patients with advanced alcoholic cirrhosis exhibited a severe deficient production of superoxide induced by the bacterial-derived peptide f-Met-Leu-Phe (fMLP) which was associated with impaired signaling (Rolas L et al, *Hepatology*, 2013). These data may explain in part the increased susceptibility of patients to bacterial infections.

Figure 3B:
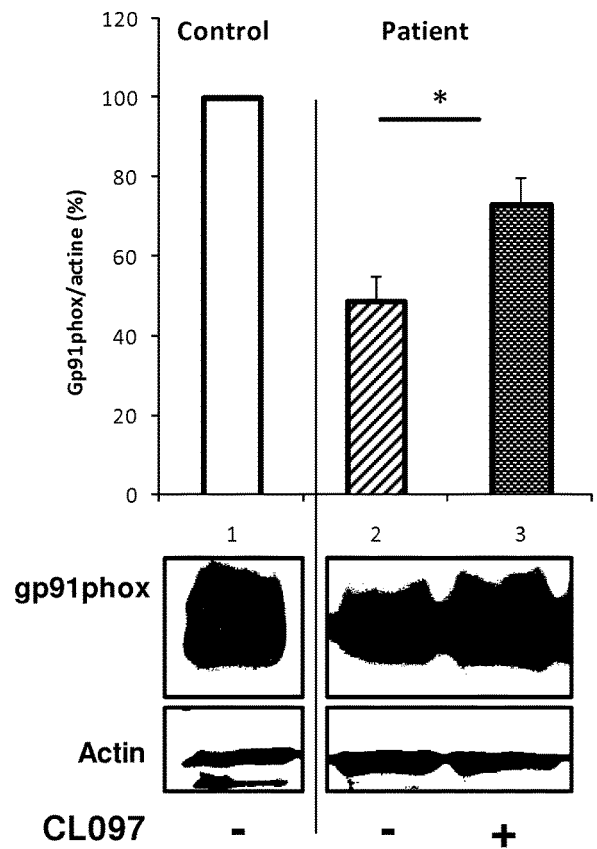

We showed here that patient neutrophils were also deficient in Gp91phox expression determined by western-blot analyses (FIGS. 2A and B), whereas the Gp91phox mRNA level was not significantly altered (FIG. 2C). Interestingly, treatment of patient neutrophils with a cell-permeable agonist of Toll-like receptors 7/8 (TLR7/8), CL097 (2.5 µg/ml, 30 min), increased Gp91phox mRNA level (FIG. 3A) and restored the expression of Gp91phox (FIG. 3B). To determine whether this treatment improves NADPH oxidase activity, superoxyde production (O2-°) was measured by the specific cytochrome C reduction assay, after cell stimulation with the bacterial peptide fMLP. Remarkably, in patient neutrophils (FIG. 4), CL097 potentiated fMLP-induced superoxide production to a level similar of that of neutrophils from healthy donors (FIG. 4), whereas CL097 further increased the optimal production of superoxide of healthy neutrophils (FIG. 4). With a more sensitive technique to quantify reactive oxygen species (ROS) such as the luminol-amplified biloluminescence assay, CL097 by itself was found to stimulate weak production of ROS and confirmed its ability to strongly potentiate fMLP-induced ROS production by patient neutrophils (FIG. 5A). Promisingly, these CL097 original properties were also observed in a model of ROS production in whole blood from patients (FIG. 5B). Finally, among other TLR7/8 agonists of the same family, R848, was more potent than CL097 to improve ROS production in whole blood from cirrhotic patients (FIG. 6B) and healthy donors (FIG. 6A).

In conclusion, the TLR7/8 agonist CL097 stimulates Gp91phox synthesis in neutrophils and potentiates ROS production induced by the bacterial peptide fMLP, providing protection against the severe deficient production of ROS mediated by advanced alcoholic cirrhosis. TLR7/8 agonists such as CL097 and R848 may thus be useful to improve antimicrobial host-defense responses of immuno-depressed patients.

Studies are developed with a rat model of cirrhosis induced by the bile duct ligation (BDL) (Mohammadi et al, 2009) treated with a CL097 analog, R848, largely used in clinical trials. The inventors provided first indication that parenteral administration of R848, also reversed the deficient ROS production in whole blood induced by cirrhosis (FIG. 11).

Example 2

Impaired Bactericidal Activity of Patients' Neutrophils and Beneficial CL097 Effects Control neutrophils incubated with *E Coli* induced significant bacterial killing (25-30%) upon stimulation with fMLP, in contrast to patients' neutrophils which were not responsive (FIG. 7A). Interestingly, CL097 alone induced significant bacterial killing by neutrophils from both controls and cirrhotic patients (FIGS. 7B and C). CL097 also strongly potentiated fMLP-induced bacterial killing by patients' neutrophils whereas a non significant increase was observed with control neutrophils (Data published by Boussif A et al, *J Hepatol.* 2016 64:1041-8. doi: 10.1016/j.jhep.2015.12.005. Epub 2015 Dec. 21, and commented by Louvet A., *J. Hepatol,* 64:1006-7, 2016). Thus, TLR7/8 activation may provide beneficial effects on neutrophil host-defense activities in patients with cirrhosis.

Example 3

A Major Role of Elastase in Mediating NOX2 Degradation in PMN

To identify proteases potentially involved in NOX2 degradation, the gp91phox sequence was subjected to in silico analysis using the MEROPS database (Rawlings et al 2014) and computer tools to predict proteases which can cleave selected substrates (Venkatraman et al 2009). Amongst the five candidates detected, elastase was the unique neutrophil protease identified. To examine its potential contribution in gp91phox degradation, a first approach was used by incubating healthy PMN for 1 H at 37° C. with purified elastase at 0.1 and 0.5 unit which provided a proteolytic activity similar to that found in degranulation supernatant (data not shown). This treatment caused gp91phox degradation by approximately 50% (FIG. 8A) with a concomitant increase of immunoreactive gp91phox fragments (Data not shown) A degradation of p22phox was observed with 0.5 unit elastase (FIG. 8B). Thus, neutrophil elastase appears to play a crucial role in gp91phox and p22phox degradation induced by fMLP. This is supported by the observation that the neutrophil elastase inhibitor MeOSuc-AAPV-CMK (commonly called NEI) prevented the fMLP-induced depletion of both components (FIGS. 8C and D). To further determine whether the gp91phox degradation process in PMN is initiated extracellularly, a cell-free supernatant of degranulating PMN was incubated with a new batch of resting PMN. This treatment also depleted gp91phox, increasing the amount of gp91phox fragments (FIG. 8E). A role of elastase in this effect is supported by the observation that PMN pretreatment with NEI blocked gp91phox degradation.

To gain insight into gp91phox external portions potentially involved in degradation process, we took profit of the gp91phox 7D5 antibody (Nakamura, 1987) which recognizes external gp91phox epitopes (loop 2 and 3), and the Biacore surface plasmon resonance (SPR) technology, to examine the real-time interaction between intact PMN and the 7D5 antibody coated on the sensor chip. As shown in FIG. 8F, injection of untreated PMN (control) resulted in a specific linear and time-dependent interaction with the 7D5 antibody. By contrast, this binding was markedly reduced in time and intensity when PMN were pretreated with elastase for 1 H at 37° C. and washed. A reduced interaction was also detected with PMN pretreated with a degranulating supernatant. These data are consistent with alterations of external epitopes and expression of gp91phox at the surface of PMN. To further examine whether elastase binds at the surface of gp91phox, PMN were treated with elastase at 4° C. for 1 H, then labeled at the same temperature with the 7D5 antibody. This treatment strongly inhibited the antibody binding assessed by FACS scan analysis (FIG. 8G), consistent with an interference effect of elastase.

Plasma from Patients with Alcoholic Cirrhosis Down-Regulate Neutrophil Production of ROS and NOX2 Expression.

Granulocyte elastase is released during infectious processes and has been proposed to be helpful for the diagnosis of patients with spontaneous bacterial peritonitis (Casafon et al., 1999), a major complication of the alcoholic liver cirrhosis. However, the relevance of plasma elastase in regulating neutrophil NOX2 activity is unknown. The amount of neutrophil elastase present in the plasma of the cirrhotic patients studied here was significantly higher than that of healthy subjects (FIG. 10), in agreement with other works (Stanley et al., 1996). To examine whether plasma elastase regulates the gp91phox expression and activity, healthy PMN were treated in the absence or presence of plasma from patients or healthy donors (control) and washed. This treatment reveals that patients' but not control plasmas decreased the amount of gp91phox positive cells labeled with the 7D5 antibody (FIG. 9A), and surface expression of gp91phox (FIGS. 9A and B). Moreover, this decrease was prevented by the elastase inhibitor NEI (FIG. 9B), strongly suggesting a contribution of patients' elastase in the gp91phox depletion. Consistent with this observation, patients' plasmas inhibited NOX2 activity of PMN measured by the cytochrome C assay (FIGS. 9C-E) and chemiluminescence. In addition, the pretreatment of plasma and PMN with NEI prevented the inhibitory effects of patients' plasma (FIGS. 9A, B and D).

REFERENCES

Throughout this application, various references describe the state of the art to which this invention pertains. The disclosures of these references are hereby incorporated by reference into the present disclosure.

The invention claimed is:

1. A method of treating bacterial infection in a patient suffering from cirrhosis comprising administering to the patient a therapeutically effective amount of a TLR7 and/or TLR8 agonist.

2. The method of claim 1 wherein the patient suffers from alcoholic liver cirrhosis, metabolic cirrhosis or viral cirrhosis.

3. The method of claim 1 wherein the patient suffers from decompensated cirrhosis.

4. The method of claim 1 wherein the bacterial infection is a bacterial peritonitis in a patient suffering from cirrhosis.

5. The method of claim 1 wherein the TLR7 and/or TLR8 agonist is selected from imidazoquinoline compounds.

6. The method of claim 1 wherein the TLR7 and/or TLR8 agonist is R848.

7. The method of claim 1 wherein the TLR7/8 agonist is incorporated in a particle appropriate for ingestion by neutrophils.

8. The method of claim 1 wherein the TLR7/8 agonist is administered concomitantly with an antibiotic.

9. The method of claim 8 wherein the antibiotic is selected from the group consisting of aminoglycosides, beta lactams, quinolones or fluoroquinolones, macrolides, sulfonamides, sulfamethaxozoles, tetracyclines, streptogramins, oxazolidinones (such as linezolid), rifamycins, glycopeptides, polymixins, and lipo-peptide antibiotics.

10. The method of claim 1 wherein the TLR7 and/or TLR8 agonist is administered in combination with an elastase inhibitor.

11. The method of claim 1 wherein the TLR7/8 agonist is not administered concomitantly with an antibiotic.

* * * * *